United States Patent [19]

Dettmeier et al.

[11] 3,948,980
[45] Apr. 6, 1976

[54] TERTIARY PHOSPHINE

[75] Inventors: Udo Dettmeier, Hurth-Hermulheim; Hans-Jerg Kleiner, Bad Soden, Taunus, both of Germany

[73] Assignee: Hoechst Aktiengesellschaft, Frankfurt am Main, Germany

[22] Filed: May 31, 1974

[21] Appl. No.: 475,275

Related U.S. Application Data

[63] Continuation of Ser. No. 171,304, Aug. 12, 1971, abandoned.

[30] Foreign Application Priority Data

Dec. 30, 1970 Germany............................ 2064574
July 7, 1971 Germany............................ 2133794

[52] U.S. Cl. ........... 260/488 J; 252/8.1; 252/389 A; 260/606.5 P; 424/212; 424/216; 424/217
[51] Int. Cl.² .............................................. C07F 9/53
[58] Field of Search.................... 260/606.5 P, 488 J

[56] References Cited

UNITED STATES PATENTS

| | | | |
|---|---|---|---|
| 3,304,263 | 2/1967 | Yoke et al. | 260/502.4 R |
| 3,716,580 | 2/1973 | Maier | 260/488 J |

FOREIGN PATENTS OR APPLICATIONS

| | | | |
|---|---|---|---|
| 1,045,604 | 3/1967 | U.S.S.R. | 260/488 J |

*Primary Examiner*—Vivian Garner
*Attorney, Agent, or Firm*—Curtis, Morris & Safford

[57] ABSTRACT

Novel tertiary phosphine oxides containing in one radical at least two hydroxy groups or functional derivatives thereof are obtained by adding olefins having at least two hydroxy groups or functional derivatives thereof to secondary phosphine oxides at elevated temperatures in the presence of a free radical generator. The products are useful as flame-retardant agents and intermediates for anti-corrosive agents and pesticides.

8 Claims, No Drawings

TERTIARY PHOSPHINE

This is a continuation of application Ser. No. 171,304, filed Aug. 12, 1971, now abandoned.

Aliphatic tertiary phoshpine oxides which carry on a carbon radical an optionally substituted hydroxy or amino group, have hitherto not been prepared or only with difficulty. A.B. Bruker et al. have succeeded in obtaining the 2-dimethyl-phosphinyl ethanol by several steps on the basis of hydroxy ethyl phosphine:

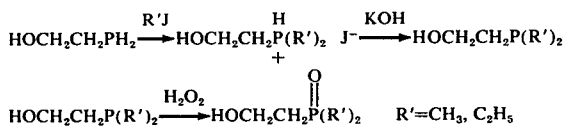

(Ž.obšč. Chim. 36 (1966), 484). This process is in no way interesting from a technical point of view.

It has now been found that tertiary phosphine oxides of the formula

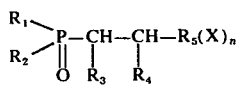

in which $R_1$ and $R_2$ are alkyl of 1 to 12 carbon atoms or cycloalkyl of 4 to 8 carbon atoms, $R_3$ is hydrogen, lower alkyl, cycloalkyl of 4 to 8 carbon atoms, or a group of the formula

in which $R_6$ is lower alkylene or cycloalkylene of 4 to 8 carbon atoms and Y is hydroxy, lower alkoxy or lower alkanoyloxy, $R_4$ is hydrogen, lower alkyl or a group of the formula

in which $R_7$ is lower alkylene and Y is as defined above, $R_5$ is a saturated aliphatic hydrocarbon radical of 1 to 5 carbon atoms and $n$ is 1 to 3, X is hydroxy, lower alkoxy, lower alkylmercapto or lower alkanoyloxy, with the proviso that in the molecule at least 2 Y are present, may be obtained with a high purity and good yields, if dialkyl phosphine oxides of the formula

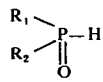

wherein $R_1$ and $R_2$ are as defined above, are reacted in the presence of catalytic amounts of free radical-forming agents and/or during exposure to ultraviolet light at a temperature between about 50° and about 250°C with olefins of the formula

wherein $R_3$, $R_4$, $R_5$ and $n$ have the above meanings.

Unless stated otherwise, the above-mentioned lower alkyl groups contain 1 to 4 carbon atoms, they may, thus, represent the methyl, ethyl, propyl or the butyl radical. Lower alkanoyl groups are acyl radicals deriving from low-molecular-weight carboxylic acids, preferably those having 1 to 5 carbon atoms, especially the formyl and the acetyl radical. In analogy to this, lower alkoxy, alkanoyloxy, alkyl mercapto and alkylene radicals are those having from 1 to 4 carbon atoms.

The dialkyl phosphine oxides used as starting materials according to the invention may be prepared according to the processes described in German Offenlegungsschriften Nos. 1,806,705, 1,806,706 and 1,806,707 and the process described in Belgian Pat. No. 737,594. The reaction according to the process of the invention proceeds particularly easily, if the dialkyl phosphine oxides are used in the very pure form as they are obtained according to the above processes.

As starting products according to the invention, the different dialkyl phosphine oxides may be employed, the alkyl groups of which contain 1 to 12, preferably 1 to 6, especially 1 to 4 carbon atoms. The alkyl groups may be straight-chained, branched or cyclic, they may be identical or different from one another. There are preferably used alkyl groups having 1 to 4 carbon atoms, that means the methyl, ethyl, propyl or butyl radical Accordingly, there may be used for example: dimethyl phosphine oxide, diethyl phosphine oxide, di-n-butyl-phosphine oxide, dicyclohexyl phosphine oxide, di-n-octyl-phosphine oxide or di-n-dodecyl-phosphine oxide.

There are preferably used olefins of the formula III, in which $R_3$ and $R_4$ represent hydrogen, lower alkyl or a group of the formula

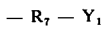

wherein $R_7$ stands for lower alkyl and Y is hydroxy, lower alkoxy or lower alkanoyloxy, $R_5$ is a bivalent or trivalent saturated aliphatic hydrocarbon radical of 1 to 5 carbon atoms, X is defined as Y and $n$ is 1 or 2.

The process according to the invention furthermore implies that olefins of the formula III are used, in which $R_3$ and $R_4$ are hydrogen, lower hydroxy alkyl or (lower alkanoyloxy)-lower alkyl, $R_5$ is a bivalent or trivalent saturated aliphatic hydrocarbon radical of 1 to 3 carbon atoms, X is hydroxy, lower alkoxy or lower alkanoyloxy and $n$ is 1 or 2, with the proviso that in the molecule 2 substituents as defined for Y are present.

The present process also implies that olefins of the formula III are employed, in which $R_3$ and $R_4$ are hydrogen, hydroxymethyl or acetoxy methyl, $R_5$ is methylene or a trivalent methane radical, X is hydroxy, acetoxy or lower alkoxy and $n$ is 1 or 2.

Olefins employable for the reaction are for example: butene-2-diol-1,4, 2-hydroxymethyl-propen-1-ol-3, pentent-2-diol-1,4, hexene-3-diol-2,5 2,5-dimethylhexene-3-diol-2,5, octene-4-diol-3,6 2-hydroxymethyl-butene-2-ol-1, hexene-1-diol-5,6, hexene-2-diol-4,5, pentene-1-diol-3,4, pentene-2-diol-4,5 and 1,2-bis-(1'-hydroxycyclohexyl)-ethylene and the methyl ethers, or acetate deriving from said olefins, which may be partially or totally etherified or esterified, such as for example 1,4-bis-acetoxy-butene-2, 1-acetoxy-4-hydroxy-butene-1-hydroxy-4-acetoxy-butene-2, 1,4-bis-methoxy-butene-2, 1-methoxy-4-acetoxy-butene-2, 1-acetoxy-4-methoxy-butene-2, 2-acetoxy-methyl-3-acetoxy-propene-1, 2-acetoxymethyl-1-propene-3-ol, 2-hydroxymethyl-3-acetoxy-propene-1, 2-methoxymethyl-1-propene-3-ol, 2-hydroxymethyl-3-methoxy-propene-1, 2-methoxymethyl-3-methoxy-propene-1, 2-methoxymethyl-3-acetoxy-propene-1 and 2-acetoxymethyl-3-methoxypropene-1;

furthermore 1-methoxy- or 1-ethoxy or 1-butoxy-2-methylpropene-2, finally acroleine-dimethyl-acetal, -diethylacetal, -dibutylacetal, pentene-(1)-al-5-dimethyl acetal, -diethyl acetal, -dipropyl acetal, 2-methyl-propene-(1)-al-3-dimethyl acetal, -diethyl acetal, moreover the different lower diacetals of 2-methylal-heptene-(1) or butene-1-al-4 and the corresponding thioacetals.

The used olefins are expediently reacted in a form as pure as possible.

The reaction is carried out at a temperature between about 50° and 250°C, preferably between about 80° and 180°C. Since the reaction is exothermic, heating is generally not required after the reaction has started. It is advantageous to carry out the reaction under protection of inert gases. As inert gases, there are considered especially argon and nitrogen, but also carbon dioxide or a hydrocarbon gas.

The free radical-forming agents are employed in catalytic amounts up to about 5 mol%, preferably about 0.1 to 1 mol%, calculated on the amount of tertiary phosphine oxide theoretically obtainable in the reaction. They are expediently dissolved in the reaction component which is slowly added in the course of the reaction.

As radical-forming agents there are considered for example:
di-tert.butyl peroxide, tert.-butyl-peroxy-benzoate, 2,5-dimethyl-hexane-bis-2, 5-(peroxybenzoate), tert.-butyl-hydroperoxide, dicumyl peroxide, azobisisobutanol diacetate, azobisisobutyronitrile, tert.-butyl-peroxyethane-nitrile-(2), tert.-butyl-peroxyethane-sulfonic acid-n-butyl ester, dibenzoyl peroxide or the like.

The free radical-forming agents are selected with regard to the temperature chosen for the reaction. Within this temperature range the radical-forming agents must have a sufficiently high half-life period. The di-tert.-butyl-peroxide and azobisisobutyronitrile are preferably employed as free radical-forming agents.

The dialkyl phosphine oxide and olefin are preferably used in a molar ratio of about 1:1. However, it is possible to use one of the reaction components in excess, for example up to the fourfold molar amount.

The reaction may also be effected in the presence of inert solvents, for example alcohols, esters and hydrocarbons. However, the reaction is preferably carried out without solvents.

The reaction according to the invention is expediently performed by adding to the dialkyl phosphine oxide the olefin, mixed with catalytic amounts of a free radical-forming agent. Olefins of a low boiling point are preferably added in the way that the supply tube leads under the surface of the dialkyl phosphine oxide. If a radical-forming agent only dissolves in the secondary phosphine oxide, a part of the whole dialkyl phosphine oxide in which this radical-forming agent is dissolved, may be added separately, besides the olefin added during the reaction.

It is also possible to introduce a tertiary phosphine oxide prepared in a first mixture, as a dissolution-promoting agent, into the reaction vessel and to add simultaneously the reaction components.

This method permits to perform the process continuously. In the same measure as olefin and secondary phosphine oxide are introduced into the reaction space, the reaction mixture is decanted. In a second reaction vessel this mixture may be kept at a definite temperature until the reaction is completed; it represents the crude tertiary phosphine oxide.

The tertiary phosphine oxides obtained according to the present process may be purified by distillation or recrystallization. They are generally obtained in very pure form. They may be employed as flame-retardant agents, as insecticides or fungicides and as corrosion inhibitors. Since the low-molecular-weight phosphine oxides are water-soluble and since the high-molecular-weight compounds exhibit surface-active properties (U.S. Pat. Nos. 3,304,263, 3,312,627, 3,325,546 and 3,332,875), the new compounds may also yield, with their reactive groups, other compounds having these properties.

After it has been known that secondary alkyl phosphine oxides have the tendency — increasing in the same measure as the number of hydrocarbon atoms in the alkyl radicals are diminuing — to be split up to form secondary phosphines and phosphine acids (Am. Soc. 77/1955, p. 3412), it has been surprising that the above reaction may be performed in the presence of radical-forming agents, especially peroxides and, above all, that it leads to good yields even at elevated temperatures from about 130° to 200° or 250°C, which due to their higher reaction speed, are interesting for technical or continuous preparation processes.

The following Examples illustrate the invention.

EXAMPLE 1

Under a nitrogen atmosphere, 215 g of 2-butene-diol-(1,4), mixed with 4 g of di-tert.-butyl-peroxide were introduced dropwise at 145° to 150°C, while stirring rapidly, in the course of 2 hours into 190 g of dimethyl phosphine oxide. The reaction product was distilled using a thin layer evaporator at 250°C and 0.02 Torr. 390 g of crude 2-dimethyl phosphinyl-butane-diol-(1,4) were obtained, which corresponds to a yield of 96.5% of the theory.

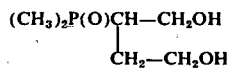

Analysis:
Calc: 43.4 % C; 9.04 % H; 18.7 % P;
Found: 44.0 % C; 9.0 % H; 18.2 % P.

EXAMPLE 2

Under a nitrogen atmosphere, 170 g of 2-hydroxymethyl-propene-1-ol-(3), mixed with 4 g of azo-bis-isobutyronitrile were introduced dropwise at 90°–120°C, while stirring rapidly, in the course of about 5 hours into 150 g of dimethyl phosphine oxide. Then the reaction product was distilled using a thin layer evaporator at 240°C and 1 Torr. 304 g of 1-dimethyl phosphinyl-2-hydroxy-methylpropanol-(3) were obtained, which corresponds to a yield of 95% of the theory.

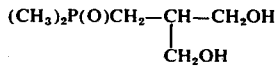

Analysis:
Calc: 43.4 % C; 9.04 % H; 18.7 % P;
Found: 43.6 % C; 9.05 % H; 18.8 % P.

EXAMPLE 3

172 g of 2-hydroxymethyl-propene-1-ol-3-diacetate were mixed with 1 g of azo-bis-isobutyronitrile and added dropwise while stirring within 2 hours to 78 g of dimethyl phosphine oxide (reaction temperature: 100°–120°C). The reaction was carried out in an inert nitrogen atmosphere. The reaction product was distilled off in a thin layer evaporator at 150°C and 2 Torr. 245 g of 1-dimethyl phosphinyl-2-hydroxymethyl-propanol-3-diacetate were obtained, which corresponds to a yield of 98% of the theory.

$$(CH_3)_2 \underset{\underset{O}{\|}}{P} CH_2 \underset{\underset{CH_2O-\underset{\underset{O}{\|}}{C}-CH_3}{|}}{\overset{CH_2O-\overset{\overset{O}{\|}}{C}-CH_3}{CH}}$$

Analysis:
Calc: 48.0 % C; 7.6 % H; 12.4 % P;
Found: 48.0 % C; 7.8 % H; 12.2 % P.

By transesterification with $CH_3OH/K_2CO_3$, the corresponding diol could be prepared from the ester.

EXAMPLE 4

138 g of dimethyl phosphine oxide were heated under nitrogen to 100°C. Within 1.5 hours, the following substances were added while stirring vigorously: 313 g of acroleine diethyl acetale and simultaneously, but separately from a second dropping funnel a mixture of 50 g of dimethyl phosphine oxide and 6 g of azobis-isobutyronitrile, which mixture was maintained at a temperature of 40°C. After dropping, stirring was continued at 100°C. After distillation 445 g of 3-dimethyl phosphinyl propionaldehyde diethyl acetale were obtained, boiling point: 125°C/0.3 Torr, which corresponds to a yield of 89 % of the theory.

Analysis: $(CH_3)_2P(O)CH_2CH_2CH(OC_2H_5)_2$
Calc: 52.0 % C; 10.1 % H; 14.9 % P;
Found: 52.1 % C; 10.2 % H; 14.7 % P.

We claim:
1. A compound of the formula

$$\underset{R_2}{\overset{R_1}{\diagdown}} \underset{\underset{O}{\|}}{P} - \underset{\underset{R_3}{|}}{C}H - \underset{\underset{R_4}{|}}{C}H - R_5 (X)_n$$

in which $R_1$ and $R_2$ are alkyl of 1 to 12 carbon atoms or cycloalkyl of 4 to 8 carbon atoms, $R_3$ is hydrogen, lower alkyl, cycloalkyl of 4 to 8 carbon atoms, or a group of the formula $$- R_6 - Y$$

in which $R_6$ is lower alkylene and Y is hydroxy, lower alkoxy or lower alkanoyloxy, $R_4$ is hydrogen, lower alkyl or a group of the formula $$- R_7 - Y$$

in which $R_7$ is lower alkylene and Y is as defined above, $R_5$ is a saturated lower alkylene radical of 1 to 5 carbon atoms and $n$ is 1 to 3, X is hydroxy, lower alkoxy, or lower alkanoyloxy, with the proviso that in the molecule at least 2 Y are present.

2. The compound as claimed in claim 1, in which $R_1$ and $R_2$ are lower alkyl, $R_3$ and $R_4$ are hydrogen, lower alkyl or a group of the formula $- R_7 - Y$, in which $R_7$ is lower alkyl and Y is hydroxy, lower alkoxy or lower alkanoyloxy, $R_5$ is a bivalent or trivalent saturated alkylene radical of 1 to 5 carbon atoms, X is defined as Y and $n$ is 1 or 2.

3. The compound as claimed in claim 1, in which $R_1$ and $R_2$ are methyl, $R_3$ and $R_4$ are hydrogen, lower hydroxyalkyl or (lower alkanoyloxy)-lower alkyl, $R_5$ is a bivalent or trivalent saturated alkylene radical of 1 to 3 carbon atoms, X is hydroxy, lower alkoxy or lower alkanoyloxy and $n$ is 1 or 2, with the proviso that in the molecule 2 substituents as defined for Y are present.

4. The compound as claimed in claim 1, in which $R_1$ and $R_2$ are methyl, $R_3$ and $R_4$ are hydrogen, hydroxymethyl or acetoxymethyl, $R_5$ is methylene or a trivalent methane radical, X is hydroxy, acetoxy or lower alkoxy and $n$ is 1 or 2.

5. The compound as claimed in claim 1, wherein $R_1$ and $R_2$ are methyl, $R_3$ is hydroxymethyl, $R_4$ is hydrogen, $R_5$ is methylene, X is hydroxy and $n$ is 1.

6. The compound as claimed in claim 1, wherein $R_1$ and $R_2$ are methyl, $R_3$ is hydrogen, $R_4$ is hydroxymethyl, $R_5$ is methylene, X is hydroxy and $n$ is 1.

7. The compound as claimed in claim 1, wherein $R_1$ and $R_2$ are methyl, $R_3$ is hydrogen, $R_4$ is acetoxymethyl, $R_5$ is methylene, X is acetoxy and $n$ is 1.

8. The compound as claimed in claim 1, wherein $R_1$ and $R_2$ are methyl, $R_3$ and $R_4$ are hydrogen, $R_5$ is a trivalent methane radical, X is ethoxy and $n$ is 2.

* * * * *